US006377833B1

(12) United States Patent  
Albert

(10) Patent No.: US 6,377,833 B1  
(45) Date of Patent: Apr. 23, 2002

(54) SYSTEM AND METHOD FOR COMPUTER INPUT OF DYNAMIC MENTAL INFORMATION

(76) Inventor: Douglas Albert, 5390 Broadway #3, Oakland, CA (US) 94618

( * ) Notice: Subject to any disclaimer, the term of this patent is extended or adjusted under 35 U.S.C. 154(b) by 0 days.

(21) Appl. No.: 09/390,048

(22) Filed: Sep. 3, 1999

Related U.S. Application Data

(60) Provisional application No. 60/117,155, filed on Jan. 25, 1999.

(51) Int. Cl.[7] .................................................. A61B 5/05
(52) U.S. Cl. .................... 600/410; 600/411; 600/425; 600/430; 600/436; 600/437; 600/451; 382/128; 250/363.01; 250/363.02; 250/363.03; 250/363.04; 345/418; 345/425
(58) Field of Search .................... 128/908; 600/545, 600/410, 407, 409, 411, 425, 430, 436, 437, 443, 444, 447, 448, 451, 463, 300, 301, 310, 383, 377, 378; 382/128–325; 250/363.01–363.04; 345/418–425

(56) References Cited

U.S. PATENT DOCUMENTS

| | | | | |
|---|---|---|---|---|
| 4,649,482 A | * | 3/1987 | Raviv et al. | 128/731 |
| 4,736,751 A | * | 4/1988 | Gevins et al. | 128/732 |
| 5,137,027 A | * | 8/1992 | Rosenfeld | 128/731 |
| 5,331,969 A | * | 7/1994 | Silberstein | 128/731 |
| 5,447,166 A | * | 9/1995 | Gevins | 128/731 |
| 5,450,855 A | * | 9/1995 | Rosenfeld | 128/732 |
| 6,104,943 A | * | 8/2000 | Frederick et al. | 600/410 |

OTHER PUBLICATIONS

B.R. Rosen et al., "Event–related functional MRI: Past, present, and future," The National Academy of Sciences, vol. 95, Feb. 1998, pp. 773–780.

G.H. Glover, "Deconvolution of Impulse Response In Event–Related BOLD fMRI1, " Academic Press, Aug. 19, 1998, pp. 416–429, url: http://www.idealibrary.com.

M.E. Raichle, "Behind the scenes of functional brain imaging: A historical and physiological perspective," The National Academy of Sciences, vol. 95, Feb. 1998, pp. 765–772.

R.B.H. Tootell et al., "Functional analysis of primary visual cortex (V1) in humans," The National Academy of Sciences, vol. 95, Feb. 1998, pp. 811–817.

(List continued on next page.)

*Primary Examiner*—Marvin M. Lateef  
*Assistant Examiner*—Jeoyuh Lin  
(74) *Attorney, Agent, or Firm*—Squire, Sanders & Dempsey, L.L.P.

(57) ABSTRACT

A system calibrates a user's brain region (e.g., the primary visual cortex or V1 region) to actual sensory information (e.g., the visual field), and enables imagined sensory information (e.g.; dynamic mental imagery) to be interpreted as computer input. The system includes a configuration engine and an input device control engine. The configuration engine includes a test pattern; a functional information gatherer for presenting the test pattern to a user; a brain-scanning device interface for obtaining functional information from a region in the user's brain that provides a physiological response to the test pattern and that receives feedback corresponding to imagined sensory information; and a mapping engine for using the functional information to map the user's brain region to the test pattern. The input device control engine includes a brain-scanning device interface for obtaining functional information from a brain region that provides a physiological response to actual sensory information and that receives feedback corresponding to imagined sensory information; an interpretation engine for interpreting the feedback; and a computer control engine for using the interpreted feedback as computer input.

71 Claims, 13 Drawing Sheets

OTHER PUBLICATIONS

B.B. Forster et al., "Functional magnetic resonance imaging: the basics of blood–oxygen–level dependent (BOLD) imaging," Canadian Association of Radiologists, vol. 49, No. 5, Oct. 1998, pp. 320–329.

W. Chen et al., "Human primary visual cortex and lateral geniculate nucleus activation during visual imagery," NeuroReport 9, vol. 9, no 16, Nov. 16, 1998, pp. 3669–3674.

B.A. Wandell, "Computational Neuroimaging Of Human Visual Cortex," Annual Reviews, Neuroscience, 1999, pp. 145–173.

H. Muller et al., "Spatial Interpolants for Wraping," Academic Press, Chapter 12, 1999, pp. 199–220.

E. Mullet et al., "Reopening the Mental Imagery Debate: Lessons from Functional Anatomy," Academic Press, Neuroimage 8, Article No. NI980355, 1998, pp. 129–139.

G. Wolberg,"Image Resampling," Digital Image Warping, Chapter 5, 1990, pp. 150–161.

G. Wolberg, "Scanline Algorithms," Digital Image Warping, Chapter 7, 1990, pp. 187–260.

G. Wolberg, "Separable Image Warping With Spatial Lookup Tables," Computer Graphics, vol. 23, No. 3, Jul. 1989, pp. 369–378.

K.M. Fant, "A Nonaliasing, Real–Time Spatial Transform Technique," IEEE CG & A, Jan. 1986, pp. 71–80.

J. Charles, "Neural Interfaces Link the Mind and the Machine," Computer, Industry Trends, Jan. 1999, pp. 16–18.

M.I. Sereno, "Borders of Multiple Visual Areas in Humans Revealed by Functional Magnetic Resonance Imaging," Science, vol. 268, May 12, 1995, pp. 889–893.

R.B.H. Tootell et al., "Functional Analysis of V3A and Related Areas in Human Visual Cortex," The Journal of Neuroscience, Sep. 15, 1997, 7 pages.

M.I. Sereno et al., Analysis of Retinotopic Maps in Extrastriate Cortex, Cerelral Cotex Nov./Dec. 1994, pp. 601–620.

S. Kosslyn, "Resolving the Imagery Debates," Image and Brain, Chapter 1, 1994, pp. 13–20.

B.A. Wandell, "Computational Neuroimaging of Human Visual Cortex," Annual Reviews Neuroscience, vol. 22, 1999, pp. 145.

P.C. Teo et al., "Creating Connected Representations of Cortical Gray Matter for Functional MRI Visualization," IEEE Transactions on Medical Imaging, vol. 16, No. 6, Dec. 1997, pp. 852–863.

H.A. Drury et al., "Computerized Mappings of the Cerebral Cortex: A Multiresolution Flattening Method and a Surface–Based Coordinate System," Journal of Cognitive Neuroscience, vol. 8, No. 1, 1996, pp. 1–28.

G.M. Boynton et al., "Linear Systems Analysis of Functional Magnetic Resonance Imaging in Human V1," The Journal Of Neuroscience, Jul. 1, 1996, pp. 4207–4221.

A.M. Dale et al., "Improved Lacalization od Cortical Activity by Combining EEG and MEG with MRI Cortical Surface Reconstruction: A Linear Approach," Journal of Cognitive Neuroscience, vol. 5, No. 2, 1993, pp. 162–176.

A. Jiang et al., "Motion Detection and Correction in Functional MR Imaging," Motion in fMRI, 1996, pp. 224–235.

R.P. Woods et al., "Rapid Automated Algorithm for Aligning and Resclicing PET Images," Journal of Computer Assisted Tomography, vol. 16, No. 4, 1992, pp. 620–633.

F. Maes et al., "Multimodality Image Registration by Maximization of Mutual Information,"60 IEEE Transactions on Medical Imaging, vol. 16, No. 2, Apr. 1997, pp. 187–198.

B. Aiazzi t al., "Pyramid–based multi–sensor image data fusion," Wavelength Applications in Signal and Image Processing V, SPIE, vol. 3169 (1997), pp. 224–235.

"Preprocessing and enhancement," A Pyramid Framework for Early Vision, pp. 64–71.

R.J.K. Jacob, "Eye Tracking in Advanced Interface Design," Virtual Environment Technologies, pp. 258–288.

S. Mori, "Historical Review of OCR Research and Development," Proceedings of the IEEE, vol. 80, No. 7, Jul. 1992, pp. 1029–1059.

J.S. Huang,"Optical Handwritten Chinese Character Recognition, " Handbook of Pattern Recognition and Computer Vision, Chapter 3.5, 1993, pp. 595–624.

R. Kasturi et al., "A System for Interpretation of Line Drawings," IEEE Transactions on Pattern Analysis and Mahine Intelligence, vol. 12, No. 10, Oct. 1990, pp. 978–992.

T. Pavlidis, "A Review of Algorithms for Shape Analysis," Compuer Vision, Graphics, and Image Processing, vol. 7, 1978, pp. 145–160.

S.M. Kosslyn et al., "Topographical representations of mental images in primary visual cortex," Nature, vol. 378, Nov. 30, 1995, pp. 496–498.

R.J. Zatorre et al., "Hearing In the Mind's Ear: A PET Investigation of Musical Imagery and Preception," Journal of Cognitive Neuroscience, vol. 8, No. 1, 1996, pp. 29–46.

C.A. Porro, "Primary Motor and Sensory Cortex Activation during Motor Performance and Motor Imagery: A Functional Magnetic Resonance Imaging Study," The Journal of Neuroscience, Dec. 1, 1996, pp. 7688–7698.

M. Roth, "Possible involvement of primary motor cortex in mentally simulated movement: a functional magnetic resonance imaging study," NeuroReport, vol. 7, No. 7, May 17, 1996, pp. 1280–1284.

* cited by examiner

Software Data-Flow Diagram for Continuous Operation

SYSTEM AND METHOD FOR COMPUTER INPUT OF DYNAMIC MENTAL INFORMATION

PRIORITY REFERENCE TO PRIOR APPLICATION

This application claims benefit of and incorporates by reference provisional patent application serial No. 60/117,155, entitled "Computer Input of Visual Mental Imagery via MRI," filed on Jan. 25, 1999, by inventor Douglas Albert.

BACKGROUND OF THE INVENTION

1. Field of the Invention

This invention relates generally to computer input devices, and more particularly provides a system and method for computer input of dynamic mental information such as visual mental imagery.

2. Description of the Background Art

Conventional computer input devices include keyboards, mice, tracker balls, touch sensitive displays and microphones. Each of these input devices translate physical actions by a user into computer instructions. For example, a computer may recognize mouse movement as a computer instruction to move a pointer and may recognize key depression on a keyboard as a computer instruction to generate text.

For physically disabled individuals who cannot control a mouse, type on a keyboard or speak into a microphone, computer input is difficult and potentially impossible. There have been several studies into the use of bioelectrical activity in the brain to control a pointer device. An article by John Charles, entitled "Neural Interfaces Link the Mind and the Machine," indicates that, by recognizing particular electrical biosignals such as electroencephalograph (EEG), electrooculograph (EOG) and electromyograph (EMG), it is possible to move a computer pointer. However, this technique does not enable computer input of text, images, sound, body movement or other sensory information to a computer.

Therefore, a system and method enabling computer input of dynamic mental information are needed.

SUMMARY OF THE INVENTION

Images on the retina are geometric mappings (projections) of what a person sees. These images are carried to a region in the visual cortex commonly referred to as the V1 region (or the primary visual cortex). The V1 region is retinotopically mapped, i.e., the physical locations of the activated neurons in the V1 region are a geometric mapping (homeomorphism) of the image on the retina. The image in the V1 region can be and has been read by using brain-scanning instruments such as functional magnetic resonance imaging (functional MRI) or positron emission tomography (PET). Neurons then carry the signals out of the V1 region and into deeper regions of the brain, which are not geometrically mapped. It has been recently recognized that there is feedback from those deeper regions back to the V1 region. It has also been recently recognized that this feedback includes images generated by the imagination. Accordingly, a system embodying the present invention reads these feedback signals to obtain and interpret this dynamic mental imagery as computer input.

It will be appreciated that other brain regions (e.g., the auditory cortex, the somatosensory cortex, etc.) may similarly provide physiological responses to other actual sensory information (e.g., sounds and voices, body movement, etc.) and may similarly receive feedback to other imagined sensory information (e.g., imagined sounds and voices, imagined body movement, etc.). Preferably, the other brain regions are large enough to distinguish content, are mapped according to a continuous sensory quantity, and receive feedback corresponding to that quantity. Accordingly, all sensory modalities could be used together to control a virtual reality system.

The system of the present invention calibrates a user's brain region (e.g., the primary visual cortex or V1 region) to actual sensory information (e.g., the visual field), and enables imagined sensory information (e.g., dynamic mental imagery) to be interpreted as computer input. The system comprises a configuration engine and an input device control engine. The configuration engine includes a test pattern; a functional information gatherer for presenting the test pattern to a user; a brain-scanning device interface for obtaining functional information from a region in the user's brain that provides a physiological response to the test pattern and that receives feedback corresponding to imagined sensory information; and a mapping engine for using the functional information to map the user's brain region to the test pattern. The input device control engine includes a brain-scanning device interface for obtaining functional information from a brain region that provides a physiological response to actual sensory information and that receives feedback corresponding to imagined sensory information; an interpretation engine for interpreting the feedback; and a computer control engine for using the interpreted feedback as computer input.

The present invention further provides a method for calibrating a user's brain region to actual sensory information, and enables imagined sensory information to be interpreted as computer input. The method comprises a configuration process and a computer input process. The configuration process includes presenting a test pattern to a user; obtaining functional information from a region in the user's brain that provides a physiological response to the test pattern and that receives feedback corresponding to imagined sensory information; and using the functional information to map the user's brain region to the test pattern. The computer input process includes obtaining functional information from a brain region that provides a physiological response to actual sensory information and that receives feedback corresponding to imagined sensory information; interpreting the feedback; and using the interpreted feedback as computer input.

The system and method of the present invention may advantageously enable computer input of imagined sensory information such as imagined images, imagined sounds, imagined body movements, etc. Accordingly, an individual unable to manipulate conventional computer input devices may be able to control a computer using only thoughts and imagination. Further, computer input of imagined sensory information may be faster than traditional computer input. Still further, since computer input is effected via the imagination, drawing ability is not as crucial.

DETAILED DESCRIPTION

Images on the retina are geometric mappings (projections) of what a person sees. These images are carried to a region in the visual cortex commonly referred to as the V1 region (or the primary visual cortex). The V1 region is retinotopically mapped, i.e., the physical locations of the activated neurons in the V1 region are a geometric mapping (homeomorphism) of the image on the retina. Mappings of the V1 region are described in Volume 95 of the *Proc. Natl. Acad. Sci. USA* (1998), entitled, "Functional Analysis of Primary Visual Cortex (V1) in Humans," by Tootell et al. The image in the V1 region can be and has been read by using brains-canning instruments such as functional magnetic resonance imaging (functional MRI) or positron emission tomography (PET). This has been described in several articles including an article in *NeuroReport* 9 (1998), pp. 3669–3674, entitled, "Human Primary Visual Cortex and Lateral Geniculate Nucleus Activation During Visual Imagery," by Chen et al. Neurons then carry the signals out of the V1 region and into deeper regions of the brain, which are not geometrically mapped. It has been recently recognized that there is feedback from those deeper regions back to the V1 region. It has also been recently recognized that this feedback includes images generated by the imagination. This recognition is described on pages 13–20 in a book entitled, "Image and Brain," by S. Kosslyn (1994), which is hereby incorporated by reference. Accordingly, a system 100 embodying the present invention reads these feedback signals to obtain and interpret this dynamic mental imagery as computer input.

It will be appreciated that other brain regions (e.g., the auditory cortex, the somatosensory cortex, etc.) may similarly provide physiological responses to other actual sensory information or stimuli (e.g., sounds and voices, body movement, etc.) and may similarly receive feedback to other imagined sensory information or stimuli (e.g., imagined sounds and voices, imagined body movement, etc.). Preferably, the other brain regions are large enough to distinguish content, are mapped according to a continuous sensory quantity, and receive feedback corresponding to that quantity. Accordingly, all sensory modalities could be used together to control a virtual reality system. Although the system 100 described below examines primarily the visual cortex, one skilled in the art will recognize that other systems that examine these other brain regions may alternatively or additionally be implemented.

Figure 1:
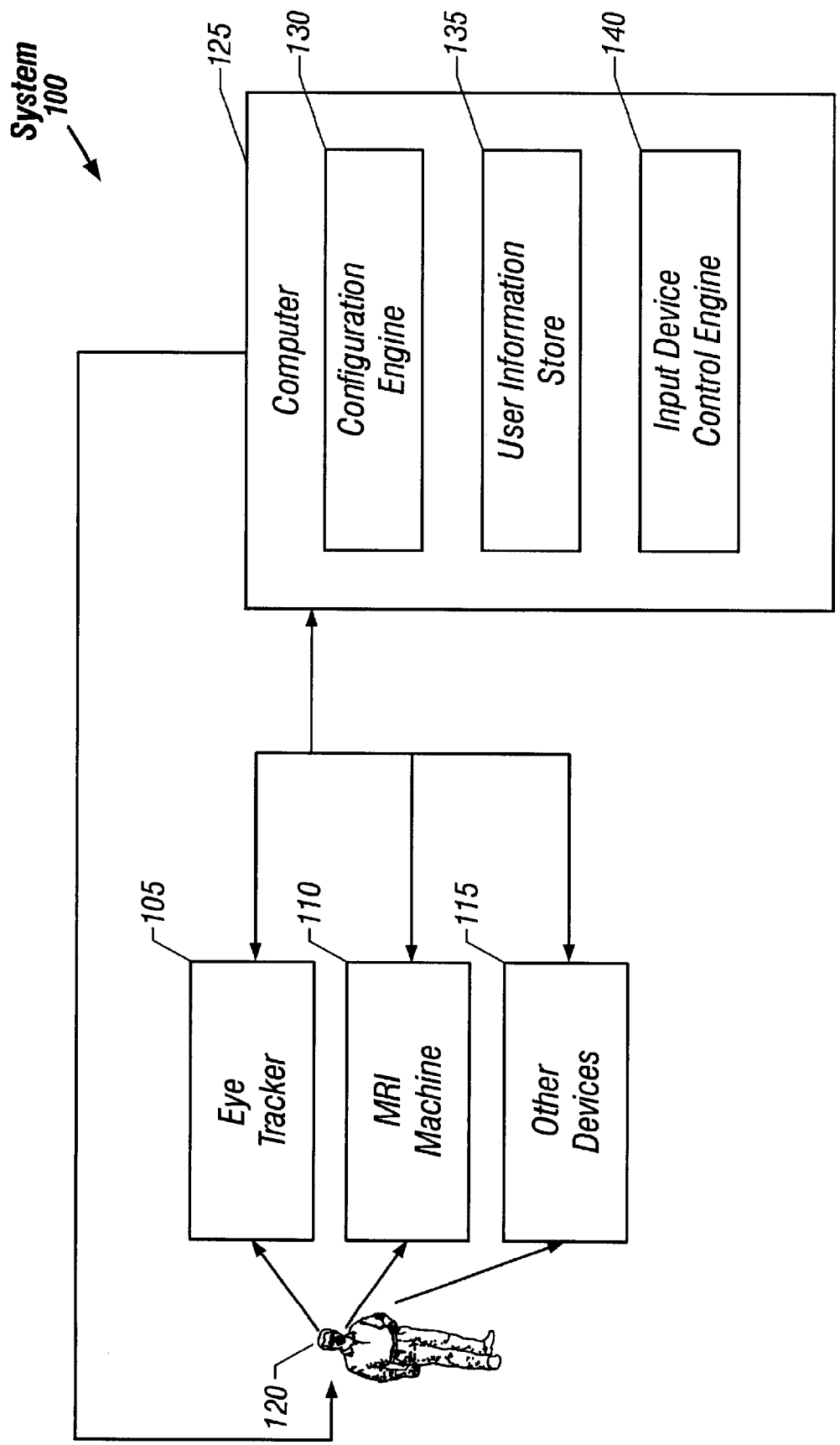
FIG. 1 is a block diagram illustrating a mental imagery computer input system, in accordance with the present invention.

FIG. 1 is a block diagram illustrating a dynamic mental imagery computer input system 100. The system 100 includes an eye tracker 105, an MRI machine 110 and other possible user-information gathering devices 115 (such as devices for recognizing muscle contraction, bioelectrical activity, breathing patterns, etc.), each coupled between a user 120 and a computer 125. The eye tracker 105, MRI machine 110 and other devices 115 gather information from the user 120, and provide the information to the computer 125. The computer 125 interprets the information from the user 120 as computer input. Although the system 100 is being described as including an MRI machine 110, one skilled in the art will recognize that other brain-scanning devices may alternatively or additionally be included.

The eye tracker 105 identifies the user's line of sight, and sends its readings to the computer 125. Based on these readings, the computer 125 determines whether the user is looking at the monitor and, if so, resolves the location on the monitor where the user is viewing. The system 100 can eliminate the eye tracker 105 if the user 120 keeps his eyes closed during computer input or uses another technique to determine when to enable or disable mental input.

The MRI machine 110 provides a noninvasive and precise technique for determining biological structures and neural activity in the user's brain. The MRI machine 110 examines magnetization, cerebral blood flow and oxygenation levels, and accordingly enables the computer 125 to generate a three-dimensional (3D) array of voxels (volume elements), commonly referred to as scans. These scans can depict structure (i.e., anatomical geometry) or function (i.e., neural activation). An example MRI is described in 1998 *Canadian Association of Radiologists*, entitled "Functional Magnetic Resonance Imaging: the Basics of Blood-Oxygen-Level Dependent (BOLD) Imaging," by Forster et al. From a series of structural and functional scans, described below, the computer 125 can generate an anatomical mapping of the user's V1 region and a physiological mapping between the user's V1 region and the user's field of view. From subsequent functional scans, described below, the computer 125 can obtain dynamic mental imagery from the user's V1 region to capture and interpret the user's visual thoughts. The MRI machine 110 may be located adjacent to the user's head such as in a headrest on the user's chair.

Preferably, the MRI machine 110 is large enough to receive information from the user's entire V1 region (e.g., about twenty square centimeters), and has high quality resolution and a high signal-to-noise ratio to allow computer recognition of detailed images. It will be appreciated that the quality of the MRI machine 110 relates to the amount of detail needed to recognize the image being viewed and/or imagined. For example, if the MRI machine 110 need only recognize Morse code, the MRI machine 110 need not be enabled to capture higher detailed images. However, to recognize English characters, Chinese characters, line drawings, shaded drawings, etc., the MRI machine 110 is preferably enabled to capture more detail. However, one skilled in the art knows that superresolution can be applied to multiple lower detailed images to generate a higher detailed image. It will be appreciated that lower power and lower resolution MRI is less expensive and less apt to be dangerous to one's health and safety. A general-purpose (i.e., entire body) medical-quality (i.e., sub-millimeter) MRI machine 110 is unnecessary.

The computer 125 includes a configuration engine 130, user information store 135 and an input device control engine 140. During configuration, the configuration engine 130 obtains and processes information gathered from the user 120, and stores the information in the user information store 135. The information gathered includes the anatomical geometry of the user's V1 region, and images read from the V1 region based on test object patterns (see FIG. 4, element 410) being presented to the user 120. The configuration engine 130 is described in greater detail with reference to FIG. 3. The user information store 135 is described in greater detail with reference to FIG. 4.

During operation, the input device control engine 140 uses the information in the user information store 135 to map dynamic mental imagery from the user's V1 region to the visual field and to interpret the dynamic mental imagery as computer input. The input device control engine 140 is described in greater detail with reference to FIG. 9. It will be appreciated that the configuration engine 130 and the input device control engine 140 may be located on different computers.

Figure 2:
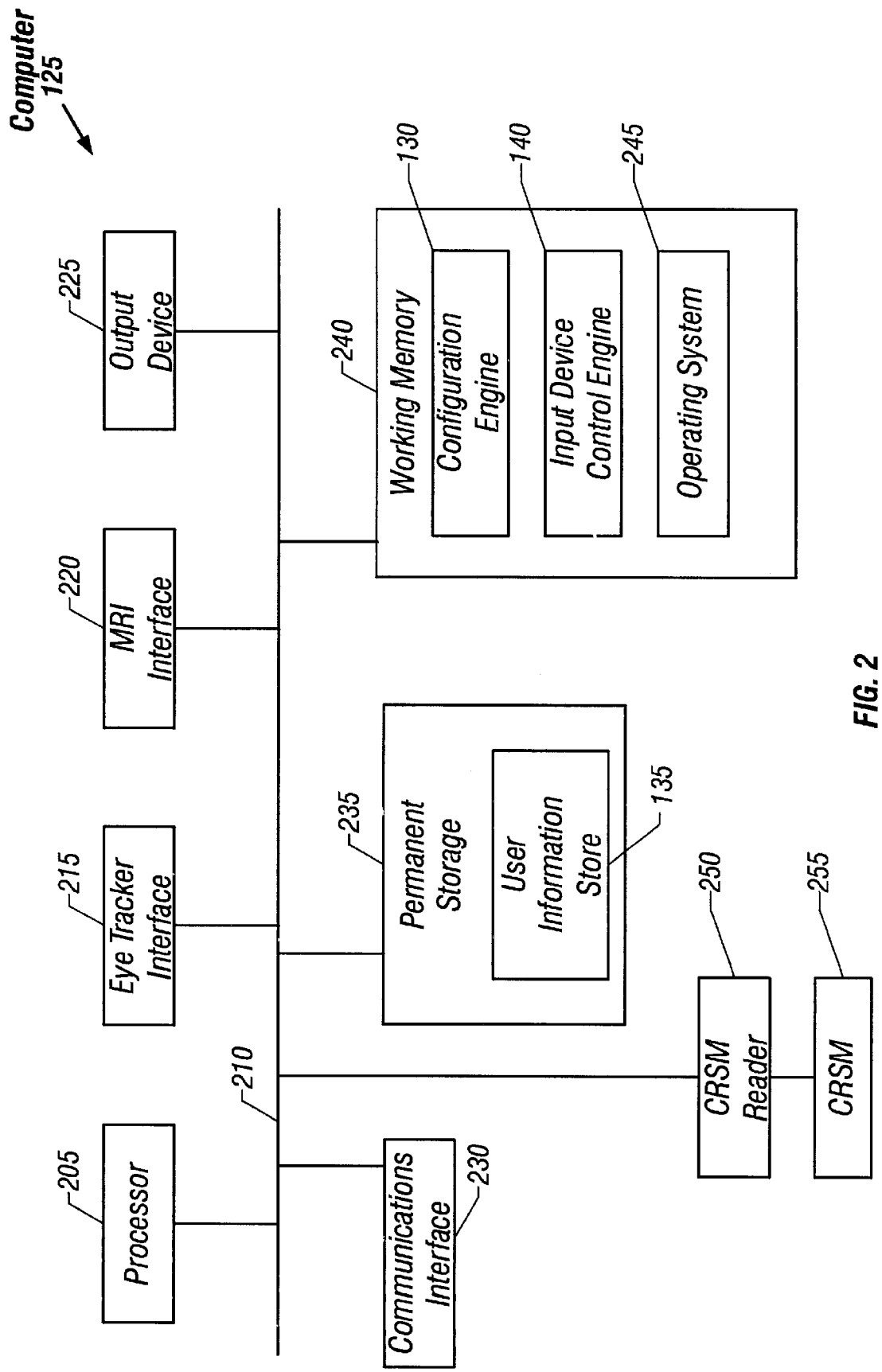
FIG. 2 is a block diagram illustrating details of the computer system of FIG.

FIG. 2 is a block diagram illustrating details of the computer 125. The computer 125 includes a processor 205, such as an Intel Pentium® microprocessor or a Motorola Power PC® microprocessor, coupled to a communications channel 210. The computer 125 further includes an eye tracker interface 215, an MRI interface 220, and an output device 225 such as a Cathode Ray Tube (CRT) display, each coupled to the communications channel 210. The computer 125 still further includes a communications device 230, permanent storage 235 such as a magnetic disk, and working memory 240 such as random-access memory (RAM), each also coupled to the communications channel 210. The communications channel 210 may be coupled to a network such as the wide-area network commonly referred to as the Internet. One skilled in the art will recognize that, although the permanent storage 235 and working memory 240 are illustrated as integral units, the permanent storage 235 and working memory 240 can be distributed units or portions of the same unit.

An operating system 245 controls processing by the processor 205, and may be stored in permanent storage 235 and loaded into working memory 240 (as illustrated) for execution. The user information store 135 may be stored in permanent storage 135 (as illustrated). The configuration engine 130 and input device control engine 140 may be stored in permanent storage 235 and loaded into working memory 240 (as illustrated) for execution. The illustrated locations of these software programs are merely exemplary and selected for ease of explanation.

One skilled in the art will recognize that the computer 125 may also include additional elements, such as network connections, additional memory, additional processors, LANs, input/output lines for transferring information across a hardware channel, the Internet or an intranet, etc. One skilled in the art will also recognize that the programs and data may be received by and stored in the system in alternative ways. For example, a computer-readable storage medium (CRSM) reader 250 such as a magnetic disk drive, hard disk drive, magneto-optical reader, CPU, etc. may be coupled to the communications channel 210 for reading a computer-readable storage medium (CRSM) 255 such as a magnetic disk, a hard disk, a magneto-optical disk, RAM, etc. Accordingly, the computer 125 may receive programs and data via the CRSM reader 250.

Figure 3:
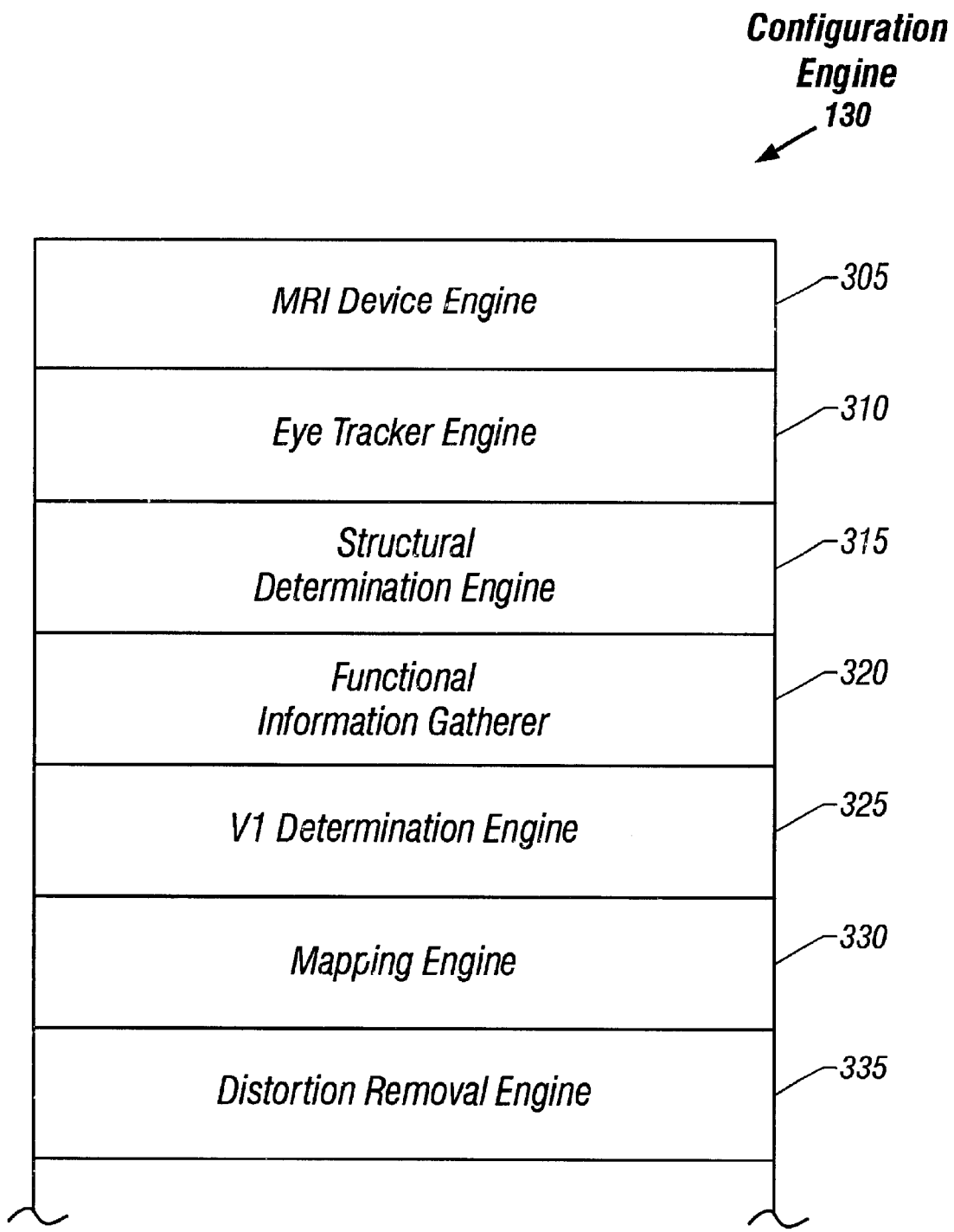
FIG. 3 is a block diagram illustrating details of the configuration engine of FIG. 1.
Figure 4:
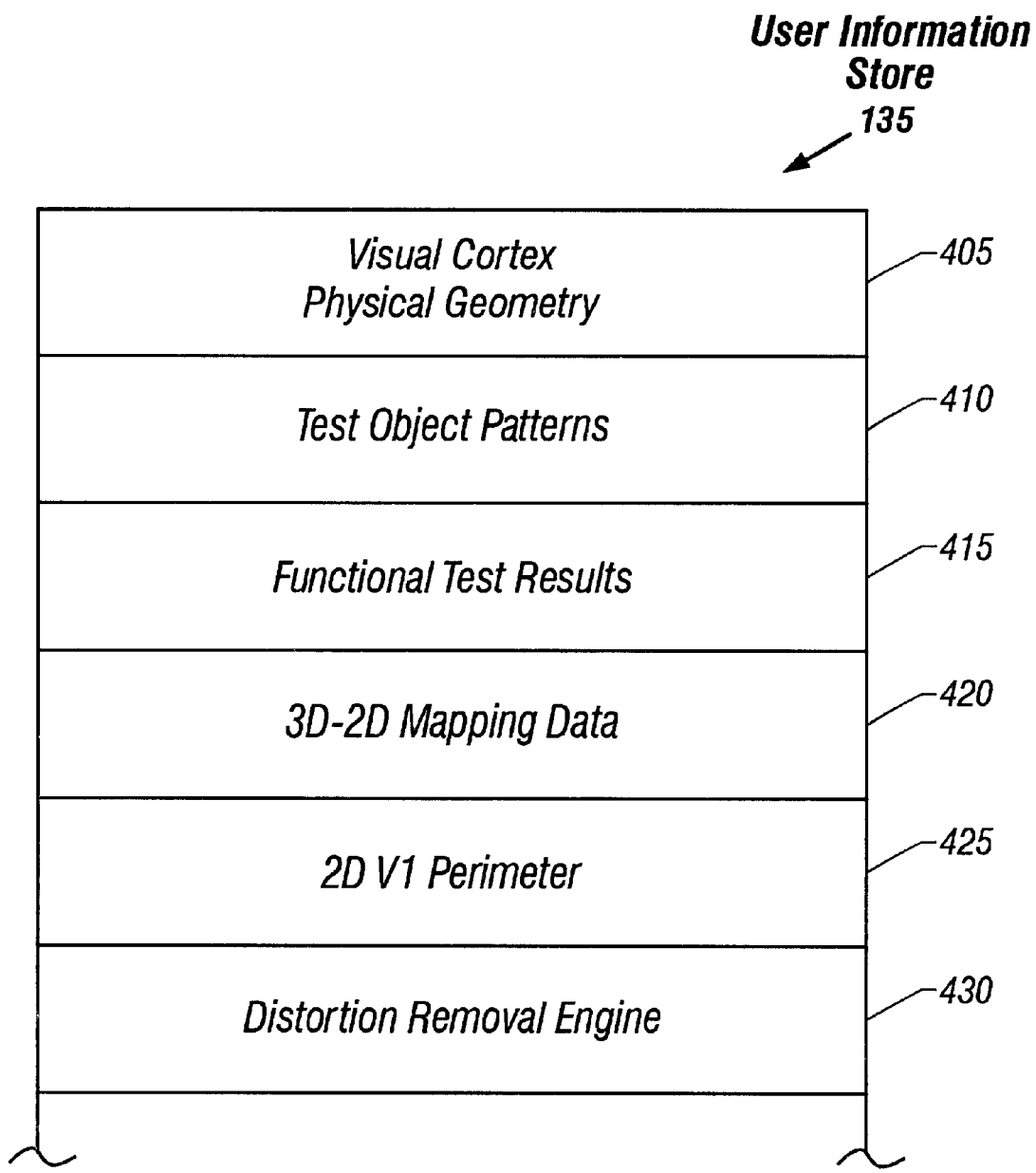
FIG. 4 is a block diagram illustrating details of the user information tables of FIG. 1.

FIG. 3 is a block diagram illustrating details of the configuration engine 130. FIG. 4 is a block diagram illustrating details of the user information store 135, which includes data used or generated by the configuration engine 130. The configuration engine 130 includes an MRI device engine 305, an eye tracker engine 310, a structural determination engine 315, a functional information gatherer 320, a V1 determination engine 325, a mapping engine 330 and a distortion removal engine 335.

The MRI device engine 305 includes the driver and interface to the MRI machine 110. The MRI device engine 305 transmits requests to the MRI machine 110 for either structural or functional scans, and receives the results back from the MRI machine 110.

The eye tracker engine 310 includes the driver and interface to the eye tracker 105. The eye tracker engine 310 transmits requests to the eye tracker 105 to track the user's line of sight, and receives the results back from the eye tracker 105.

The structural determination engine 315 instructs the MRI device engine 305 to request a structural scan from the MRI machine 110, and receives the results of the scan back from the MRI machine 110 via the MRI device engine 305. As stated above, the results enable the structural determination engine 315 to generate a three-dimensional (3D) anatomical image of the user's visual cortex (which includes several regions including the V1 region). The 3D anatomical image of the user's visual cortex is stored in the user information store 135 as visual cortex physical geometry 405. As is well known in the art, the cerebral cortex can be effectively read by scanning the 2D boundary layer between the grey and white matter of the brain. Locating the grey/white boundary layer in a structural scan is described in "Creating Connected Representations of Cortical Gray Matter for Functional MRI Visualization," by Teo and Wandell, *IEEE Trans. Medical Imaging*, v.16, n.6 (1997), pages 852–863.

The structural determination engine 315 then unfolds the visual cortex, i.e., converts the 3D visual cortex image into two dimensions. Computing the transformation of the 3D layer into 2D is described in "Computerized Mappings of the Cerebral Cortex: A Multiresolution Flattening Method and a Surface-Based Coordinate System," by Drury et al, J. Cognitive Neuroscience, v.8, n.1, (1996) pages 1–28. The structural determination engine 315 then stores the transformation function in the user information store 135 as 3D–2D mapping data 420. The V1 determination engine 325 and the dynamic V1 determination engine 920 can subsequently use the stored 3D–2D mapping data 420 to produce 2D images of neural activation from 3D functional scans.

In more detail, the 3D–2D mapping data 420 can be specified as a triples function such as $S[i,j]=(a,b,c)$ where S represents a warping function, $[i,j]$ represents a pixel location in the output 2D image, and $(a,b,c)$ represents the corresponding point in the input 3D scan. The V1 determination engine 325 and the dynamic V1 determination engine 920 use interpolation to handle points lying between voxels in the input 3D scan due to warping. An example function S and interpolation algorithms are described in detail in Chapter 5 of *Digital Image Warping* by G. Wolberg, which is hereby incorporated by reference. The structural determination engine 315 stores the 3D–2D transformation function S into the user information store 135 as 3D–2D mapping data 420. One skilled in the art knows that, although the function S and interpolation are being described as algorithms, the information may be tables, matrices, diagrams, plots, graphs, or any other transformation function.

It will be appreciated that, during configuration, the MRI machine 110 preferably performs the structural scan of the user's V1 region while the user faces directly forward.

Figure 5A:
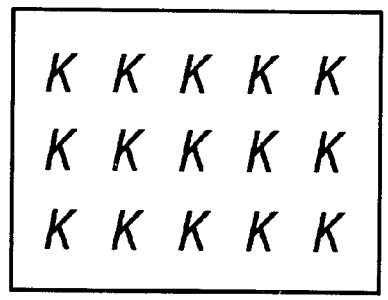
FIG. 5A illustrates an example test object pattern of FIG. 4.
Figure 5B:
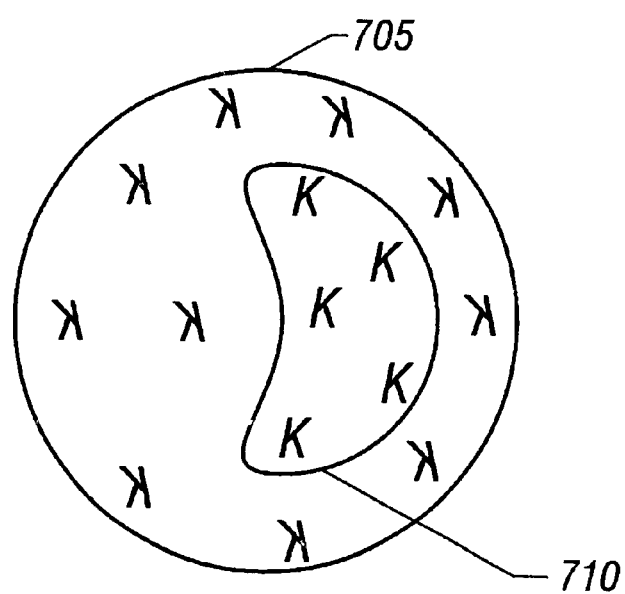
FIG. 5B illustrates example details of the V1 geometry of FIG. 5A within the visual cortex.

The functional information gatherer 320 displays a test object pattern 410 on the output device 225, and instructs the MRI device engine 305 to request a functional scan. FIG. 5A illustrates an example test object pattern 410' as a single image frame containing an array pattern of the letter "K". Although not shown, the test object pattern 410' can also include the environment surrounding the viewable region of the display device 225 and within the user's peripheral vision. Further, the test object pattern 410' can alternatively be multiple frames or a more complex image, such as the sequence of images illustrated in FIG. 6, discussed below. While the user 120 looks at the test object pattern 410, the MRI machine 110 reads and forwards the pattern of neural activation in the user's visual cortex to the MRI device engine 305. The functional information gatherer 320 obtains and stores the pattern of neural activation in the user information store 135 as functional test results 415. FIG. 5B illustrates example functional test results 415' from the MRI machine 110 in response to the example test object pattern 410'. It will be appreciated that test object patterns 410 may be sounds, voices, movements, etc. based on the brain region being examined and the sensory information being interpreted.

The V1 determination engine 325 includes a mapping engine that examines the functional test results 415 to determine the perimeter of the user's V1 region. More particularly, the V1 determination engine 325 obtains the functional test results 415 from the functional information gatherer 320 or from the user information store 135. The test object pattern 410 in the user information store 135 may be only the image being displayed on the output device 225. Alternatively, the test object pattern 410 in the user information store 135 may have been resolved from images obtained by a digital still/video camera (not shown). The V1 determination engine 325 uses the 3D–2D mapping data 420 to transform the function test results 415' onto a flat 2D plane, as described above. The V1 determination engine 325 compares the test object pattern 410' against these transformed test results to determine the 2D perimeter of the user's V1 region.

As illustrated in FIG. 5B, the image obtained by the MRI machine 110 from the V1 region 710 has the original orientation and the image in the visual cortex 705 outside the V1 region 710 has the reverse orientation. Accordingly, the V1 determination engine 325 examines image orientation to determine the 2D perimeter of the V1 region within the user's visual cortex. Preferably, the perimeter of the V1 region may be located by computing gradient vectors and visual field signs. If the test object pattern 410' included the sequence of images illustrated in FIG. 6, the V1 determination engine 325 would also examine virtual rotational direction to determine the 2D perimeter of the user's V1 region. For example, a sequence of images virtually rotating clockwise would appear to rotate clockwise in the user's V1 region and appear to rotate counter-clockwise outside the user's V1 region. The V1 determination engine 325 stores the 2D perimeter of the user's V1 region in the user information store 135 as 2D V1 perimeter 425.

Figure 6:
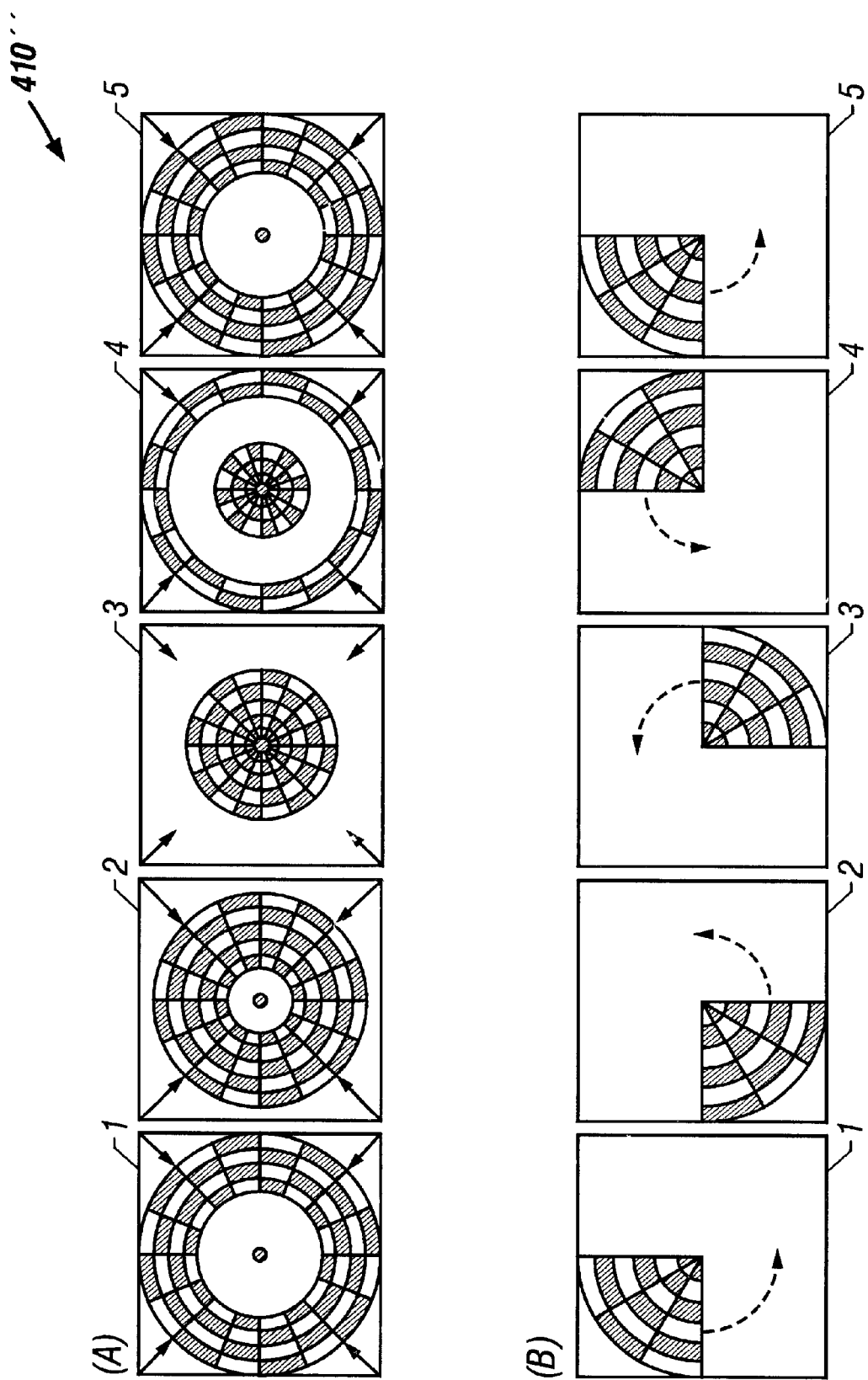
FIG. 6 illustrates other example test object patterns of FIG. 4.
Figure 7:
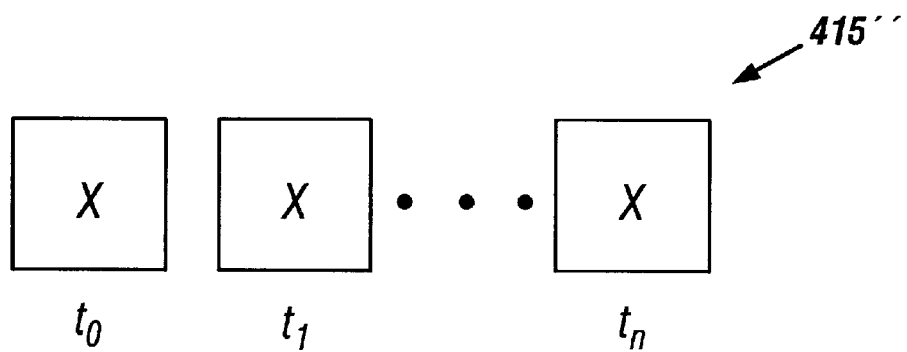
FIG. 7 illustrates example function test results of FIG. 6.

It has been discovered that the V1 region magnifies objects near the center of the user's gaze and relatively reduces the size of objects near the periphery of the user's gaze. This is referred to as "the cortical magnification factor" or "CMF." Accordingly, the configuration engine 130 contains a distortion removal engine 335 that computes magnification removal tables, algorithms or any other transformation function. This distortion removal engine 335 measures this distortion in the following manner:

The functional information gatherer 320 further displays test object patterns 410 onto the output device 225, and instructs the MRI device engine 305 to request a functional scan. FIG. 6 illustrates example test object patterns 410", shown as a first sequence labeled "A" and a second sequence labeled "B." Patterns 1–5 of sequence A show a series of concentric checkerboard rings contracting inward. Patterns 1–5 of sequence B show a series of checkerboard quarter-circles rotating counter-clockwise. These patterns are discussed in greater detail in an article entitled, "Computational Neuroimaging of Human Visual Cortex," in the *Neuroscience Annual Review*, V.22 (1999), pages 145–173, which is hereby incorporated by reference. The functional information gatherer 320 stores the results from the functional scan in the user information store 135 also as functional test results 415. FIG. 7 illustrates additional details of the functional test results 415 obtained while the user 120 looks at one of the test object patterns 410", such as sequence A or sequence B. The functional test results 415 are illustrated as a sequence of images from time $t_0$ to time $t_n$. It will be appreciated that, although sequences A and B are described as visual sequences, the sequences may be sounds, voices, body movements, etc. based on the brain region being examined and the sensory information being interpreted.

More particularly, if sequence A includes a periodic contraction frequency, each pixel in the plane will have an intensity that varies periodically as a function of time. By taking the Fast Fourier Transform (FFT) of each pixel's intensity, a peak frequency can be recognized at the contraction frequency of the test sequence. The phase of this contraction frequency component yields the eccentricity r, i.e., the distance from the center of the user's field of view. Similarly, since sequence B has periodic spinning motion, each pixel in the plane will also have an intensity that varies periodically as a function of time. By taking the Fast Fourier Transform (FFT) of each pixel's intensity, a peak frequency can be recognized at the rotation frequency of the test sequence. The phase of this rotation frequency component provides the angle from the horizontal plane of the corresponding point in the user's field of view. This technique enables the correlation of points in the V1 region to points in the user's field of view.

The distortion removal engine 335 includes a mapping engine that computes magnification removal algorithms or tables from the phases described above. The distortion removal engine 335 stores the algorithms or tables in the user information store 135 as distortion removal data 430. Distortion removal data 430 is subsequently used by the dynamic distortion removal engine 925 to remove cortical magnification factor from dynamic mental images.

In more detail, the distortion removal data 430 can be specified as a 2D array of pairs (x,y)=F[i,j], where (i,j) represents a pixel in the distorted image, (x,y) represents a point in the undistorted image, and F is a distortion removal function computed from the phases described above. The dynamic distortion removal engine 925 uses interpolation to handle points lying between pixels in the undistorted image due to warping. An example function F and interpolation algorithms are described in greater detail in an article entitled, "Spatial Interpolants for Warping," by Muller and Ruprecht, published as Chapter 12 of *Brain Warping*, ed. Arthur W. Toga (1999).

Figure 8:
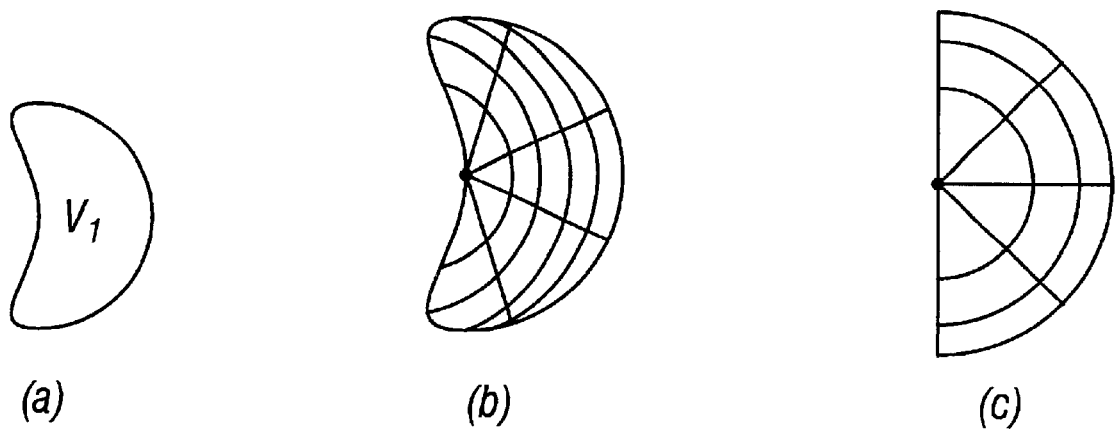
FIG. 8 illustrates example distortion removal algorithms of FIG. 4.

FIG. 8 illustrates magnification removal. Image (a) shows the V1 region as a two-dimensional "distorted" region. Image (b) shows the V1 region divided into sections in accordance with cortical magnification. Image (c) shows the V1 region divided into sections without cortical magnification. The distortion removal engine 335 stores the coordinate mapping tables or algorithms and magnification removal tables or algorithms in the user information store 135 as distortion removal data 430. One skilled in the art knows that, although the distortion removal data 430 is being described as tables or algorithms, the distortion removal data 430 may be matrices, diagrams, plots, graphs or any other transformation function.

It will be appreciated that the mapping and distortion removal data will be different based on the brain regions being examined, the sensory information being interpreted, the format being used to represent the sensory information, etc. For example, if the sensory information is voices and sound, then the sensory information format would be a chronological order of musical notes and guttural utterances.

Figure 9A:
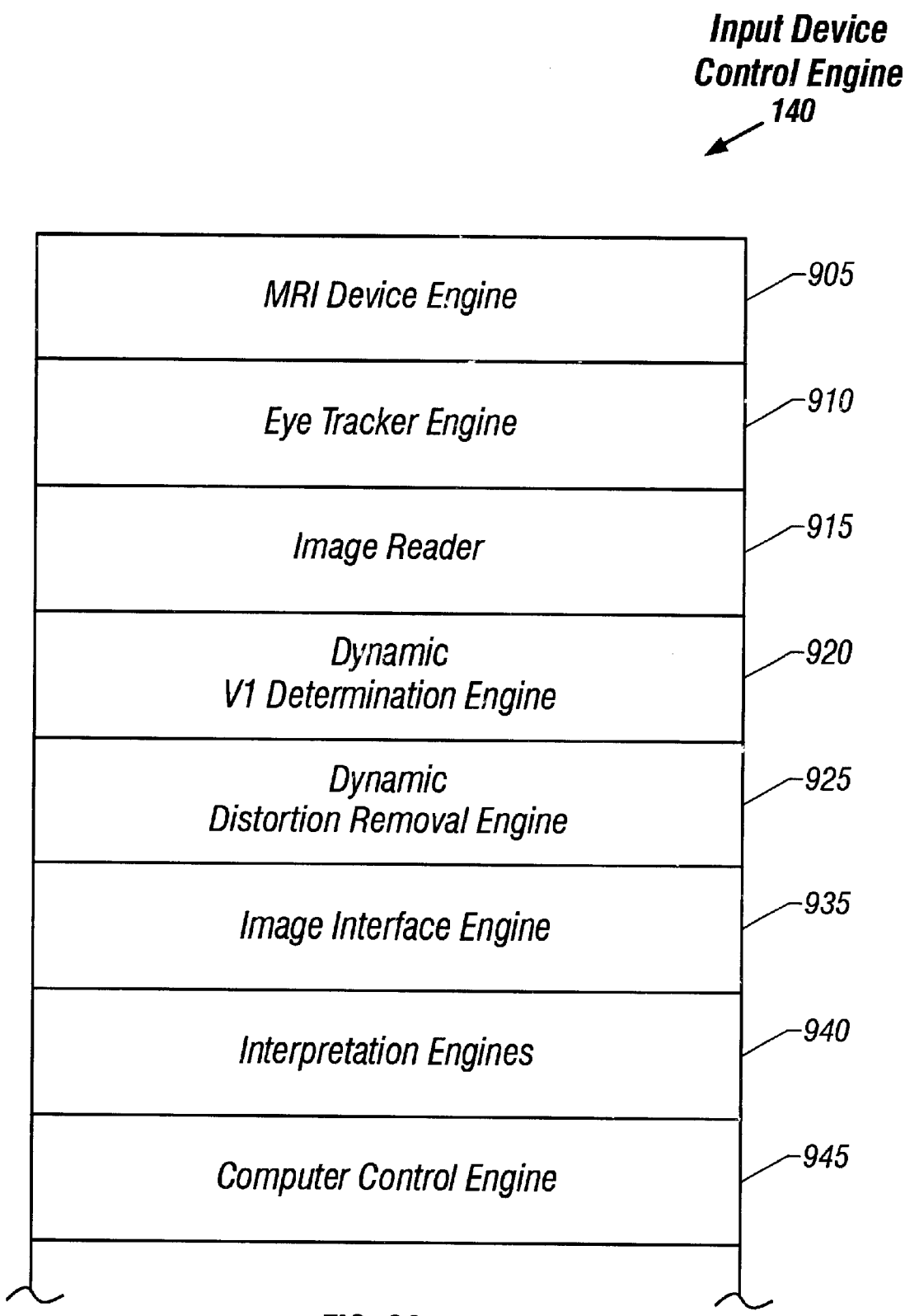
FIG. 9A is a block diagram illustrating details of the input device control engine of FIG. 1.

FIG. 9 is a block diagram illustrating details of the input device control engine 140. The input device control engine 140 includes an MRI device engine 905, an eye tracker engine 910, an image reader 915, a dynamic V1 determination engine 920, a dynamic distortion removal engine 925, an image inference engine 935, interpretation engines 940 and a computer control engine 945.

The MRI device engine 905 is similar to the MRI device engine 305 and includes the driver and interface to the MRI machine 110. The MRI device engine 905 transmits requests to the MRI machine 110 for either structural or functional scans, and receives the results back from the MRI machine 110.

The eye tracker engine 910 is similar to the eye tracker engine 310 and includes the driver and interface to the eye tracker 105. The eye tracker engine 910 transmits requests to the eye tracker 105 to track the user's line of sight, and receives the results back from the eye tracker 105.

The image reader 915 instructs the MRI device engine 905 to request the MRI machine 110 to perform a functional scan, and receives the results back from the MRI device engine 905. The image reader 915 uses the results to generate a 3D functional image (i.e., dynamic mental imagery) from the user's visual cortex. The image reader 915 may use a time sequence of 3D functional images to generate a single useful 3D functional image. It will be appreciated that there are multiple ways to control activation of the image reader 915. For example, the image reader 915 may instruct the eye tracker engine 910 to request the eye tracker 105 to obtain line of sight information. The image reader 915 may instruct the MRI device engine 905 to request a functional scan only when the user 120 is looking at the output device 225. Alternatively, the image reader 915 may instruct the MRI device engine 905 to request a functional scan only when the user's eyes are closed longer than an average blink time. Other possible activation techniques are also possible.

The dynamic V1 determination engine 920 resolves the current angular position of the user's head. More particularly, the dynamic V1 determination engine 920 compares the 3D functional image (which contains physical anatomy) obtained by the image reader 915 against the 3D visual cortex physical geometry 405 stored in the user information store 135. The V1 determination engine 920 rotates the 3D functional image until it matches most closely with the physical geometry 405. Based on the angular results, the V1 determination engine 920 rotates the 3D functional image to obtain a motion-corrected 3D functional image. If the V1 determination engine 920 cannot match the 3D functional image to the physical geometry 405, then the V1 determination engine 920 may instruct the MRI device engine 905 to request the MRI machine 110 to perform a new structural scan. The V1 determination engine 920 may also request re-calibration based on the new structural scan.

The dynamic V1 determination engine 920 uses the 3D-2D mapping data 420 stored in the user information store 135 to map the 3D functional image obtained from the user's visual cortex into 2D. The dynamic V1 determination engine 920 includes a mapping engine that uses the 2D V1 perimeter 425, which is stored in the user information store 135 and described with reference to FIG. 3, to identify the user's V1 region within the 2D functional image.

The dynamic distortion removal engine 925 includes a mapping engine that uses the distortion removal data 430, which is stored in the user information store 135 and described above with reference to FIG. 3, to remove the distortion from the 2D functional image generated by the dynamic V1 determination engine 920. Accordingly, the dynamic distortion removal engine 925 generates a 2D undistorted functional image of the user's visual and imagined dynamic mental imagery. The undistorted functional image includes the user's visual field image being viewed and/or imagined.

The image inference engine 935 infers the image being viewed by the user 120. The image inference engine 935 instructs the eye tracker engine 910 to request the eye tracker 105 to determine whether the user 120 has opened or closed eyes. If the user's eyes are closed, then, in a first embodiment, the inference engine 935 may infer that the user sees nothing. Alternatively, in a second embodiment, the image inference engine 935 may assume the image being viewed is the previous image imagined. The user 120 can accordingly build on previous images. For example, the user 120 can imagine a table and then a chair with the table. Despite the eyes being closed, the inferred image in the second embodiment would be the table. If the user's eyes are opened, then, in a third embodiment, the inference engine 935 may presume that the image being viewed is the image displayed on the output device 225. In yet a fourth embodiment, the inference engine 935 may obtain the image being viewed by requesting line sight information from the eye tracker 105, and resolving the image being viewed from external information received from a digital still/video camera (not shown). Other embodiments are also possible in light of the foregoing teaching.

The interpretation engines 940 compare the inferred image with the visual representation of the functional image to determine the differences, i.e., the imagined portion of the functional image. The interpretation engines 940 interpret the imagined portion. To interpret the imagined image more accurately, the interpretation engines 940 may include an engine for interpreting Morse code, an engine for interpreting English characters, an engine for interpreting Chinese characters, an engine for interpreting line drawings, an engine for interpreting shaded drawings, etc. It will be appreciated that a more specific interpretation engine 940 will better recognize imagined images. Assuming that the expected image is an English alphabet character, the English alphabet interpretation engine 940 compares the imagined image against possible characters, and selects the one that most closely matches the imagined image as the interpreted image.

The computer control engine 945 uses the interpreted image as computer input. For example, the computer control engine 945 may be an interface to a word processor program. The computer control engine 945 may construe the interpreted image as an instruction such as "Save," or as data to be inserted into the document. Many modes of computer control are possible in light of the foregoing teachings. For example, the interpreted image may be construed as text data, graphical data, computer instructions, menu item selection, desktop item selection, mouse-down events, pointer control, etc. It will be appreciated that the computer control engine 945 may instruct the eye tracker engine 910 to request the eye tracker 105 to obtain line of sight information. The computer control engine 945 may construe the line of sight information as position information indicating where on a document to place the imagined image.

It will be appreciated that the system 100 may also use visual information as computer input. For example, if image reader 915 is active when the user 120 is looking at the output device 225, an object brought into the user's line of sight may be considered input. It will also be appreciated that, when the image reader 915 is active when the user 120 is looking at the output device 225, an object brought into the user's line of sight will have substantially greater intensity, clarity and consistency than an imagined object. Accordingly, the interpretation engines 940 can easily discard these objects.

Figure 9B:
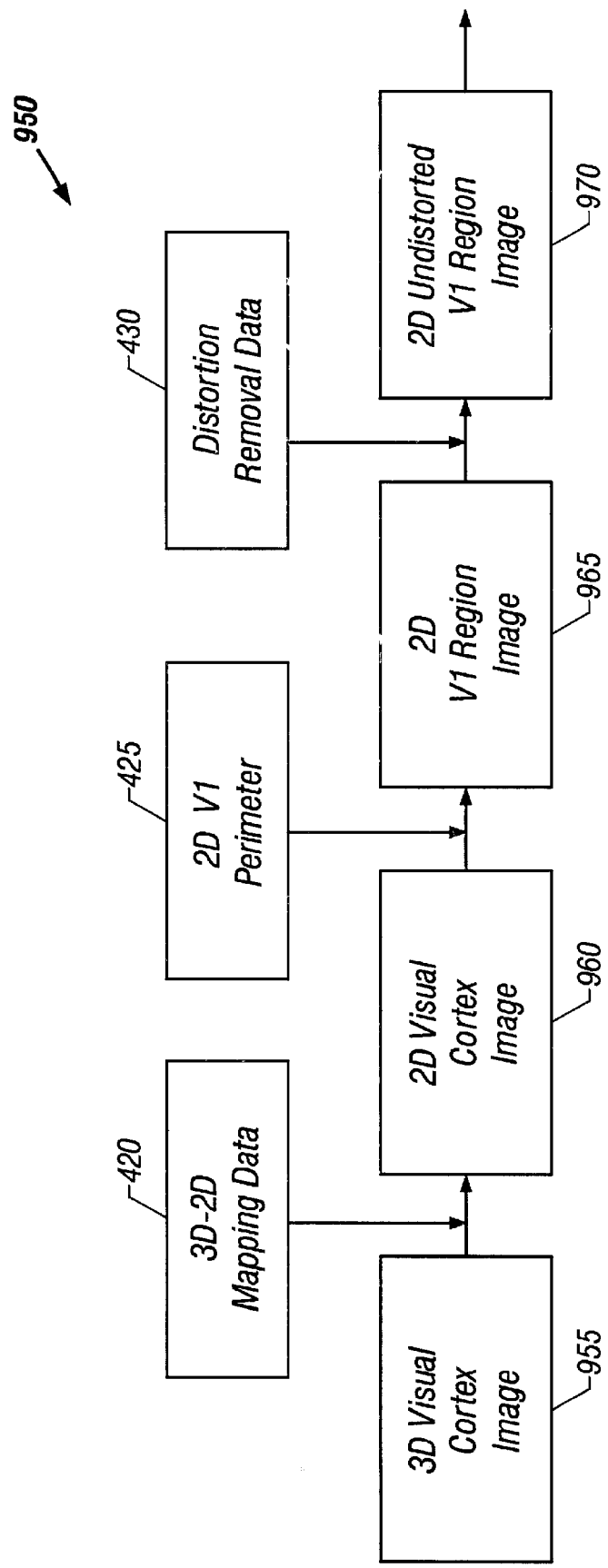
FIG. 9B is a block diagram illustrating translation of a 3D visual cortex image to a 2D visual-field-mapped image.

FIG. 9B is a block diagram illustrating translation of a 3D visual cortex image 955 to a visual-field-mapped image 970. The MRI machine 110 obtains the 3D visual cortex image 955. The V1 dynamic determination engine 920 uses the 3D–2D mapping data 420 to map the 3D visual cortex image 955 into a 2D visual cortex image 960. The dynamic V1 determination engine 920 uses the 2D V1 perimeter 425 to identify the perimeter of the 2D V1 region image 965 within the 2D visual cortex image. The distortion removal engine 925 uses the distortion removal data 430 to remove the distortion in the 2D V1 region image 965, thereby generating a 2D undistorted V1 region image 970.

Figure 10:
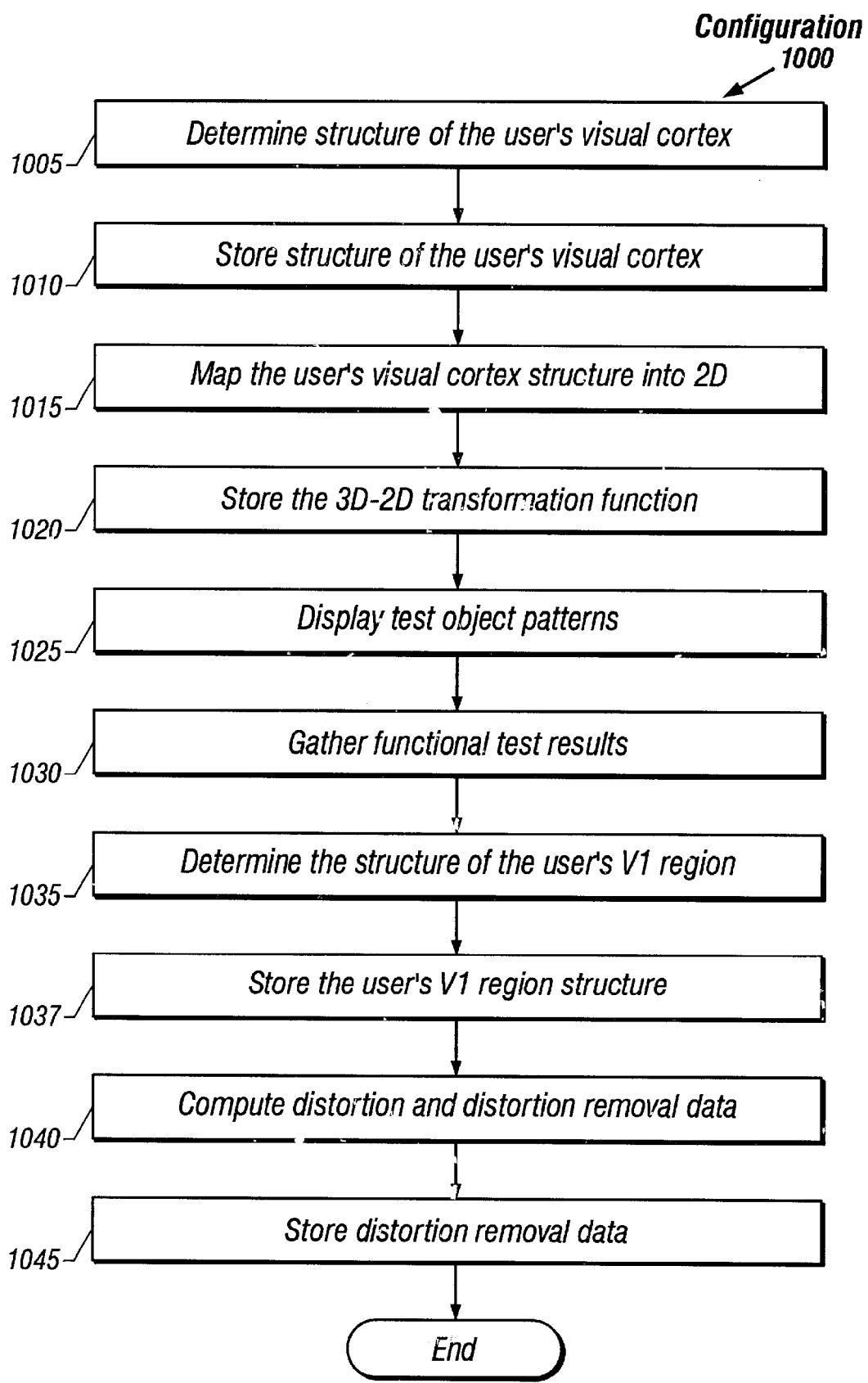
FIG. 10 is a flowchart illustrating a method of configuring a mental imagery computer input device, in accordance with the present invention.

FIG. 10 is a flowchart illustrating a method 1000 of configuring the system 100, in accordance with the present invention. Method 1000 begins with the structural determination engine 315 in step 1005 determining the 3D anatomical structure of the user's visual cortex. The structural determination engine 315 in step 1010 stores the anatomical structure in the user information store 135 as visual cortex physical geometry 405.

The structural determination engine 315 in step 1015 uses triples and mapping algorithms to map the 3D geometry 405 into 2D, and in step 1020 stores the 3D-to-2D transformation function in the user information store 135 as 3D–2D mapping data 420.

The functional information gatherer 320 in step 1025 displays test object patterns 410 on the output device 225. Example test object patterns 410 are illustrated in FIGS. 5A and 6. While the user 120 views the test object patterns 410, the functional information gatherer 320 in step 1030 obtains the results and stores them in the user information store 135 as functional test results 415.

The V1 determination engine 325 in step 1035 examines the functional test results 415 to determine the 2D perimeter of the user's V1 region. As stated above, one technique for determining the perimeter of the V1 region includes examining image orientation within the visual cortex. The V1 determination engine 325 in step 1037 stores the user's V1 region perimeter in the user information store 135 as 2D V1 perimeter 425.

The distortion removal engine 335 in step 1040 computes the distortion, e.g., the cortical magnification factor (CMF), and accordingly computes distortion removal data. FIG. 8 illustrates distortion removal. The distortion removal engine 335 in step 1045 stores the distortion removal data 430 in the user information store 135. Method 1000 then ends.

Figure 11A:
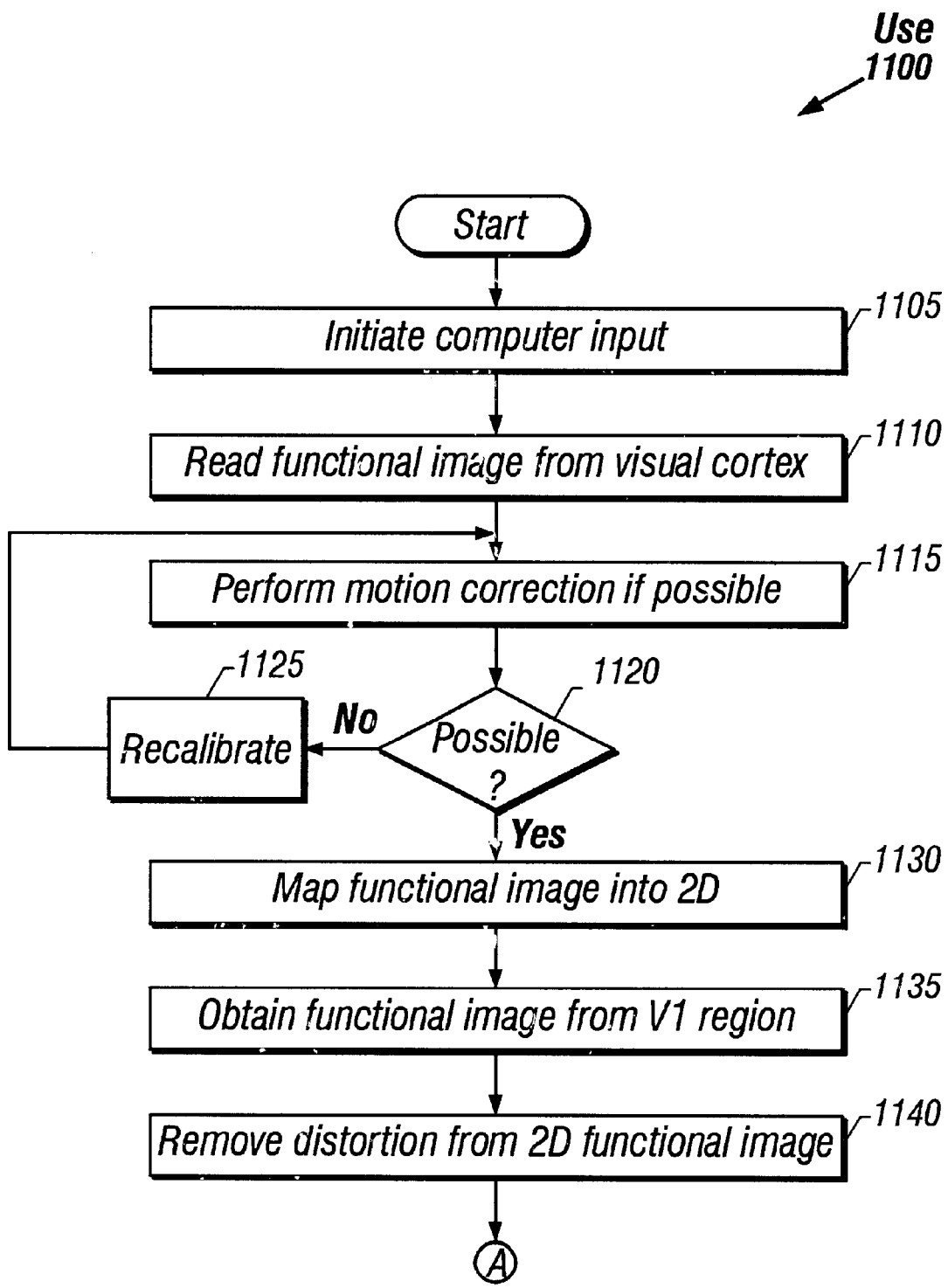
FIGS. 11A and 11B are a flowchart illustrating a method of controlling a computer using MRI, in accordance with the present invention.
Figure 11B:
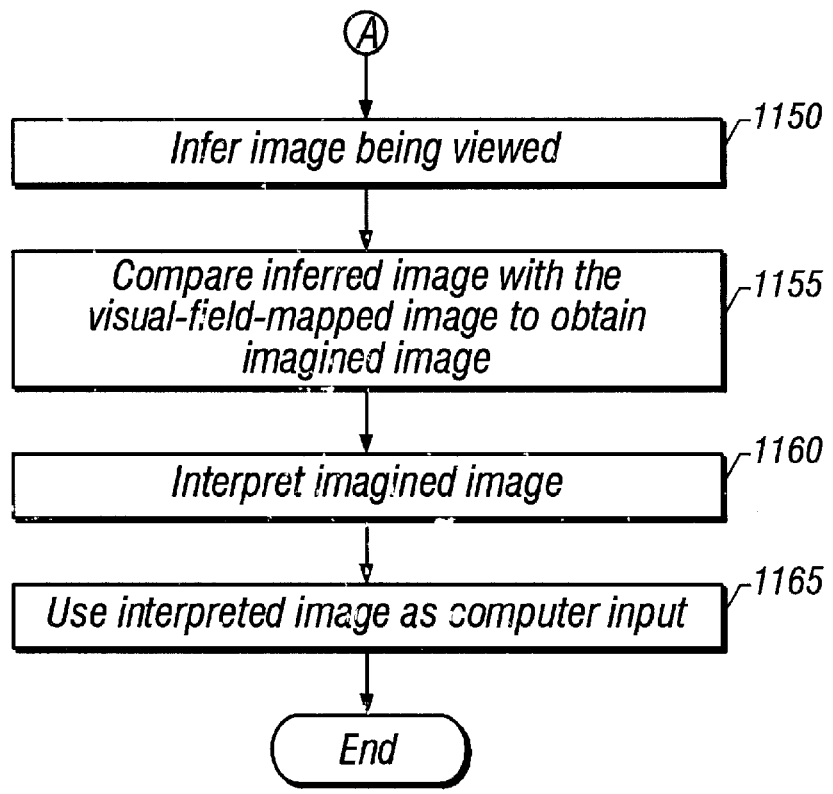

FIGS. 11A and 11B are a flowchart illustrating a method 100 of computer input. Method 1100 begins with the image reader 915 in step 1105 determining whether to initiate computer input. The image reader 915 may instruct the eye tracker engine 910 to request the eye tracker 105 to obtain line of sight information, and, if the user 120 is currently looking at the output device 225, then the image reader initiates computer input. The image reader 915 in step 1110 instructs the MRI device engine 905 to request the MRI machine 110 to perform a functional scan of the user's visual cortex. The MRI machine 110 obtains and forwards the 3D visual cortex image 955 via the MRI device engine 905 to the image reader 915. The dynamic V1 determination engine 920 in step 1115 performs motion correction, if possible. That is, the dynamic V1 determination engine 920 compares a structural element in the 3D visual cortex image 955 against the visual cortex physical geometry 405 to determine the amount of rotation (along a vertical or horizontal plane). The V1 determination engine 920 in step 1120 determines whether the V1 determination engine 920 successfully obtained the motion correction. If the dynamic V1 determination engine 920 cannot determine the amount of rotation, then the dynamic V1 determination engine 920 in step 1125 requests the configuration engine 130 to re-calibrate (i.e., re-determine the data stored in the user information store 135).

If the dynamic V1 determination engine 920 in step 1120 determines that motion correction was computed successfully, then the dynamic V1 determination engine 920 in step 1130 applies the motion correction to the 3D visual cortex image 955 and uses the 3D–2D mapping data 420 to map the motion-corrected 3D visual cortex image 955 into a 2D visual cortex image 960. The V1 determination engine 920 in step 1135 uses the 2D V1 perimeter 425 to determine the 2D V1 region image 965, and then obtains the functional image from the 2D V1 region image 965.

The distortion removal engine 925 in step 1140 uses the distortion removal data 430 to remove the distortion from the 2D V1 region image 965 and generate a 2D undistorted V1 region image 970.

The image inference engine 935 in step 1150 infers the image being viewed by the user 120. That is, the image inference engine 935 may instruct the eye tracker engine 910 to request the eye tracker 105 to determine whether the user's eyes are shut. If so, then the image inference engine 935 may infer that the image being viewed is nothing. Accordingly, any image in the user's visual cortex is an imagined image. Alternatively, the image inference engine 935 may infer that the image being viewed was the last image in the user's visual cortex. For example, if the user thinks of a first image, which is transmitted to the display, the second image being considered may be an addition to the previously imagined image. Accordingly, the user 120 can build onto imagined images. If not, then the image inference engine 935 may infer that the image is the image being displayed on the output device 225 or an image obtained from a digital still/video camera (not shown).

The interpretation engines 940 in step 1155 compare the inferred image with the 2D undistorted V1 region (visual-field-mapped) image 970 to determine the differences, i.e., the imagined portion of the image 970. Again, the imagined portion may be the entire image 970 or elements replacing portions of the image 970. The interpretation engines 940 in step 1160 interpret the imagined portion. Preferably, the interpretation engines 940 include various engines for recognizing different types of data such as English characters, Chinese characters, directional arrows, shaded drawings, line drawings, etc. The computer control engine 945 uses the interpreted image as computer input. For example, the computer engine 945 may use the interpreted image as text data to be input to a word processor, graphical data to be input to a drawing program, directional data identifying the direction to move a pointer, etc. Method 1100 then ends.

Figures 12A, 12B:
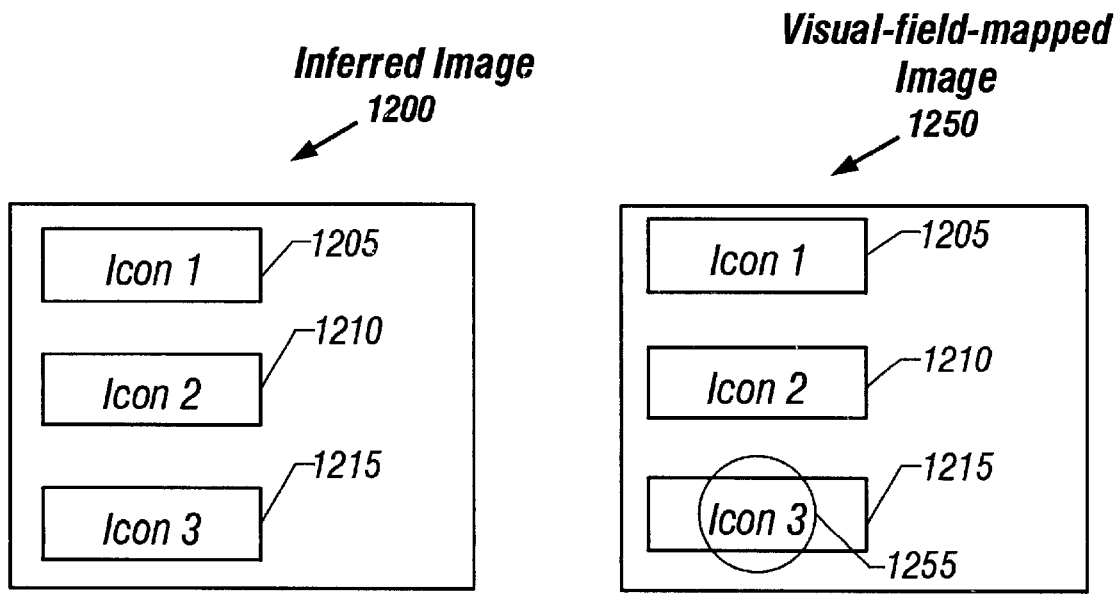
FIG. 12A illustrates an example inferred image of FIG. 9.
FIG. 12B illustrates an example interpreted image of FIG. 9.

FIG. 12A illustrates an inferred image 1200, which includes a first icon ("Icon 1") 1205, a second icon ("Icon 2") 1210 and a third icon ("Icon 3") 1215. FIG. 12B illustrates a visual-field mapped image 1250, which includes the first icon ("Icon 1") 1205, the second icon ("Icon 2") 1210, the third icon ("Icon 3") 1215 and a shaded circle 1255 covering the third icon ("Icon 3") 1215. The interpretation engines 940 would compare the inferred image 1200 with the visual-field-mapped image 1250 to determine that the only difference is the covering of the third icon ("Icon 3") 1215 with the shaded circle 1255. The computer control engine 945 may recognize the imagined shaded circle 1255 as selection of the third icon 1215.

Figure 13:
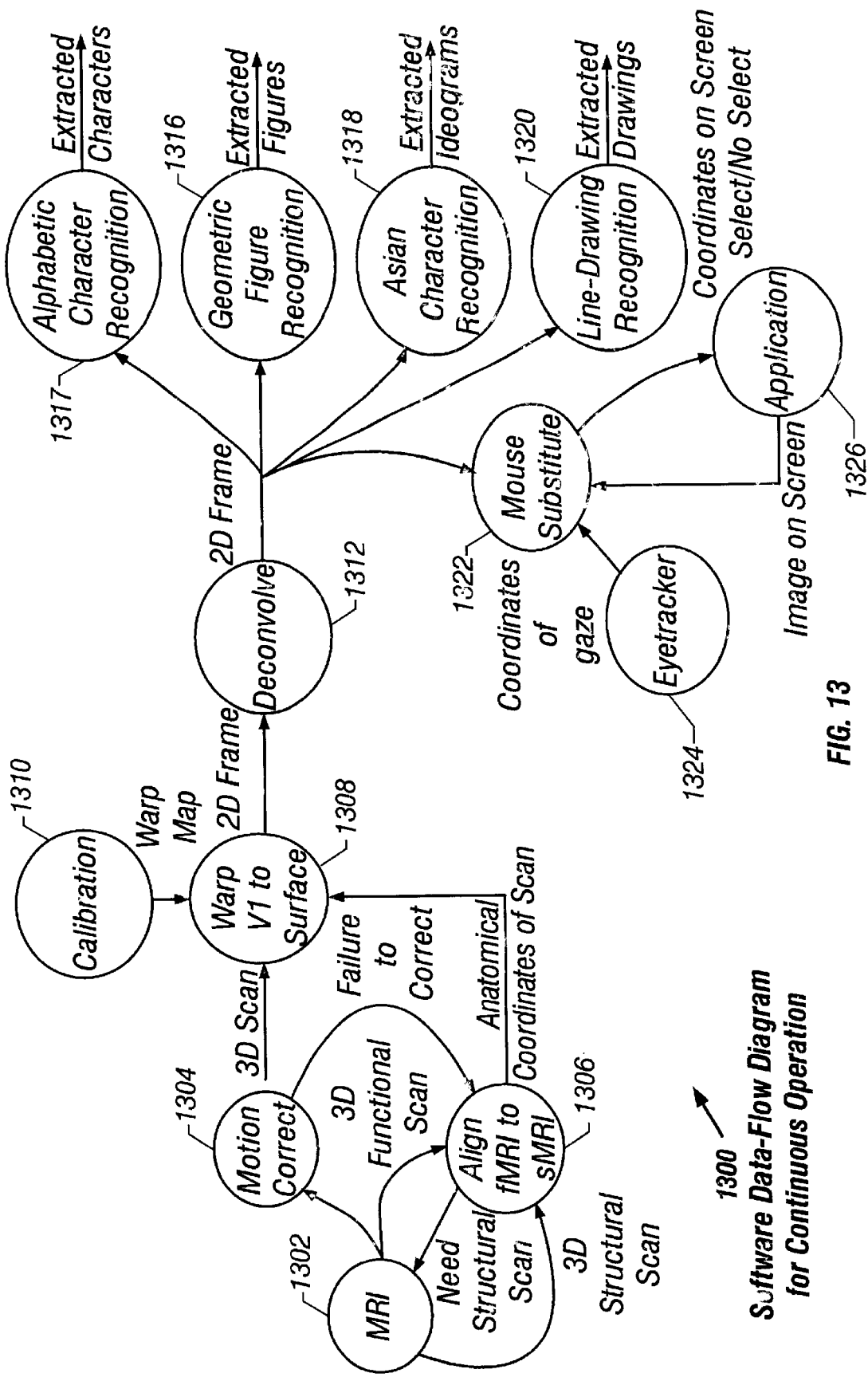
FIG. 13 illustrates a data flow diagram of a method for controlling computer input, in accordance with the present invention.

FIG. 13 is a software data-flow diagram 1300 illustrating continuous operation of the input device control engine 140. The diagram 1300 begins at node 1302 by performing a functional scan. The 3D functional image obtained by the functional scan is sent to node 1304 for motion correction. If motion correction fails, then at node 1306 re-alignment of the functional image (fMRI) to the structural image (sMRI) is requested. That is, a new structural scan is requested at node 1302, and the results sent to node 1306. The anatomical coordinates of the scan are then sent to node 1308. If motion correction is successful, then the 3D scan is sent to node 1308.

At node 1308, the 3D scan is warped to the visual field using the warp map (i.e., the 3D–2D mapping data 420, the distortion removal data 430 and the 2D V1 perimeter data 425) obtained from the calibration stage 1310). The 2D visual image is sent to node 1312 for deconvolution. That is, the 2D image may be time reviewed (e.g., multiple frames may be reviewed to obtain a clearer picture), time delayed (e.g., to wait for sufficient blood oxygen response to occur), and/or compared with other sensors (e.g., magnetic sensors, breathing sensors, eye trackers, etc.). For example, after viewing and imagining images, the blood oxygen levels take time to change. Accordingly, a slow rise in the blood oxygen level may represent a single spike.

The 2D visual image may be interpreted in accordance with alphabetic character recognition at node 1314 (the character extracted being transmitted to the appropriate application program), with geometric figure recognition at node 1316 (the geometric figure being transmitted to the appropriate application program), with Asian character recognition at node 1318 (the ideogram extracted being transmitted to the appropriate application program) or with line-drawing recognition at node 1320 (the drawing extracted being transmitted to the appropriate application program). One skilled in the art knows that other recognition engines are also possible. In one embodiment, the 2D visual image may be used as a mouse substitute at node 1322. For example, the pointer may be controlled by an eye tracker at node 1324, and the coordinates of the gaze sent to node 1322. In another embodiment, the application at node 1326 may send the image on the screen to the node 1322, and the mouse substitute engine may compare the 2D visual image against the image on the screen. Based on the comparison, the coordinates on the screen or a select/no-select instruction may be determined.

The foregoing description of the preferred embodiments of the present invention is by way of example only, and other variations and modifications of the above-described embodiments and methods are possible in light of the foregoing teaching. Although the nodes are being described as separate and distinct nodes, one skilled in the art will recognize that these nodes may be a part of an integral node, may each include portions of multiple nodes, or may include combinations of single and multiple nodes. Further, components of this invention may be implemented using a programmed general purpose digital computer, using application specific integrated circuits, or using a network of interconnected conventional components and circuits. Connections may be wired, wireless, modem, etc. Still further, although some transformation functions are being described as algorithms or tables, one skilled in the art will recognize that other functions such as matrices, diagrams, plots, graphs or other functions are also possible. The embodiments described herein are not intended to be exhaustive or limiting. The present invention is limited only by the following claims.

What is claimed is:

1. A computer-implemented method, comprising:
   obtaining functional information from a user's brain region that provides a physiological response to actual sensory information and that receives feedback from at least one other brain region, the feedback corresponding to imagined sensory information;
   interpreting the feedback; and
   using the interpreted feedback as computer input.

2. The method of claim 1, wherein the brain region includes the visual cortex.

3. The method of claim 1, wherein the brain region includes the auditory cortex.

4. The method of claim 1, wherein the brain region includes the somatosensory cortex.

5. The method of claim 2, wherein the brain region includes the V1 region.

6. The method of claim 1, further comprising mapping the functional information to a corresponding sensory information format.

7. The method of claim 6, further comprising obtaining mapping data for mapping the functional information to the corresponding sensory information format.

8. The method of claim 7, wherein the brain region includes V1 region, the actual sensory information includes visual field data, and imagined sensory information includes imagined visual field data.

9. The method of claim 8, wherein the sensory information format includes the user's visual field.

10. The method of claim 9, wherein the mapping data includes 3D to 2D mapping data.

11. The method of claim 10, wherein the mapping data includes perimeter data for identifying the V1 region within the user's visual cortex.

12. The method of claim 7, further comprising removing distortion from the functional data.

13. The method of claim 12, wherein removing distortion includes removing cortical magnification.

14. The method of claim 13, wherein the mapping data includes distortion removal data.

15. The method of claim 1, further comprising using a functional MRI machine to capture the feedback.

16. The method of claim 15, further comprising using an eye tracker to enable and disable the MRI machine.

17. The method of claim 16, further comprising enabling the MRI machine when the eye tracker determines that the user is looking a particular direction.

18. The method of claim 1, further comprising comparing the functional information with structural information of the brain region to perform motion correction.

19. A system, comprising:
   a brain-scanning device interface for obtaining functional information from a user's brain region that provides a physiological response to actual sensory information and that receives feedback from at least one other brain region, the feedback corresponding to imagined sensory information;
   an interpretation engine for interpreting the feedback; and
   a computer control engine for using the interpreted feedback as computer input.

20. The system of claim 19, wherein the brain region includes the visual cortex.

21. The system of claim 19, wherein the brain region includes the auditory cortex.

22. The system of claim 19, wherein the brain region includes the somatosensory cortex.

23. The system of claim 20, wherein the brain region includes the V1 region.

24. The system of claim 19, further comprising a mapping engine for mapping the functional information to a corresponding sensory information format.

25. The system of claim 24, wherein the mapping engine obtains mapping data for mapping the functional information to the corresponding sensory information format.

26. The system of claim 25, wherein the brain region includes V1 region, the actual sensory information includes visual field data and the imagined sensory information includes imagined visual field data.

27. The system of claim 26, wherein the sensory information format includes the user's visual field.

28. The system of claim 27, wherein the mapping data includes 3D to 2D mapping data.

29. The system of claim 28, wherein the mapping data includes perimeter data for identifying the V1 region within the user's visual cortex.

30. The system of claim 25, further comprising a distortion removal engine for removing distortion from the functional data.

31. The system of claim 30, wherein the distortion removal engine removes cortical magnification.

32. The system of claim 31, wherein the mapping data includes distortion removal data.

33. The system of claim 19, further comprising an MRI device engine for requesting a functional MRI machine to capture the feedback.

34. The system of claim 33, further comprising an image reader for enabling and disabling the MRI machine.

35. The system of claim 34, wherein the image reader enables the MRI machine when the eye tracker determines that the user is looking a particular direction.

36. The system of claim 19, further comprising a dynamic V1 determination engine for comparing the functional information with structural information of the brain region to perform motion correction.

37. A system, comprising
   means for obtaining functional information from a user's brain region that provides a physiological response to actual sensory information and that receives feedback from at least one other brain region, the feedback corresponding to imagined sensory information;
   means for interpreting the feedback; and
   means for using the interpreted feedback as computer input.

38. A computer-readable storage medium storing program code for causing a computer to perform the steps of:
   obtaining functional information from a user's brain region that provides a physiological response to actual sensory information and that receives feedback from at least one other brain region, the feedback corresponding to imagined sensory information;
   interpreting the feedback; and
   using the interpreted feedback as computer input.

39. A computer-implemented method, comprising:
   presenting a test pattern to a user;
   obtaining functional information from a region in the user's brain that provides a physiological response to the test pattern and that receives feedback from at least one other brain region, the feedback corresponding to imagined sensory information; and
   using the functional information to map the user's brain region to the test pattern.

40. The method of claim 39, wherein the test pattern includes visual imagery.

41. The method of claim 39, wherein the test pattern includes sound.

42. The method of claim 39, wherein the test pattern include body movement.

43. The method of claim 39, wherein the test pattern includes a sequence of visual images.

44. The method of claim 39, wherein the test pattern includes a visual image and the surrounding environment.

45. The method of claim 39, wherein the user's brain region includes the visual cortex.

46. The method of claim 45, wherein the user's brain region includes the V1 region.

47. The method of claim 39, wherein the user's brain region includes the auditory cortex.

48. The method of claim 39, wherein the user's brain region includes the somatosensory cortex.

49. The method of claim 39, further comprising obtaining structural information of the user's brain region.

50. The method of claim 49, further comprising using an MRI machine.

51. The method of claim 49, further comprising mapping the structural information into 2D structural representation.

52. The method of claim 51, further comprising generating distortion removal data for removing distortion from the 2D structural representation.

53. The method of claim 52, wherein removing distortion includes removing cortical magnification.

54. A system, comprising:
   a test pattern;
   a functional information gatherer for presenting the test pattern to a user;
   a brain-scanning device interface for obtaining functional information from a region in the user's brain that provides a physiological response to the test pattern and that receives feedback from at least one other brain region, the feedback corresponding to imagined sensory information; and
   a mapping engine for using the functional information to map the user's brain region to the test pattern.

55. The system of claim 54, wherein the test pattern includes visual imagery.

56. The system of claim 54, wherein the test pattern includes sound.

57. The system of claim 54, wherein the test pattern include body movement.

58. The system of claim 54, wherein the test pattern includes a sequence of visual images.

59. The system of claim 54, wherein the test pattern includes a visual image and the surrounding environment.

60. The system of claim 54, wherein the user's brain region includes the visual cortex.

61. The system of claim 60, wherein the user's brain region includes the V1 region.

62. The system of claim 54, wherein the user's brain region includes the auditory cortex.

63. The system of claim 54, wherein the user's brain region includes the somatosensory cortex.

64. The system of claim 54, wherein the brain-scanning device interface further obtains structural information of the user's brain region.

65. The system of claim 64, wherein the brain-scanning device interface includes a functional MRI device engine.

66. The system of claim 65, further comprising a mapping engine for mapping the structural information into 2D structural representation.

67. The system of claim 66, further comprising a distortion removal engine for generating distortion removal data for removing distortion from the 2D structural representation.

68. The system of claim 67, wherein removing distortion includes removing cortical magnification.

69. A system, comprising:

means for presenting a test pattern to a user;

means for obtaining functional information from a region in the user's brain that provides a physiological response to the test pattern and that receives feedback from at least one other brain region, the feedback corresponding to imagined sensory information; and means for using the functional information to map the user's brain region to the test pattern.

70. A computer-readable storage medium storing program code for causing a computer to perform the steps of:

presenting a test pattern to a user;

obtaining functional information from a region in the user's brain that provides a physiological response to the test pattern and that receives feedback from at least one other brain region, the feedback corresponding to imagined sensory information; and using the functional information to map the user's brain region to the test pattern.

71. A computer-implemented method, comprising:

obtaining functional information from a user's brain region that provides a physiological response to actual sensory information and that receives feedback from at least one other brain region, the feedback corresponding to imagined sensory information;

obtaining inferred information from a camera;

generating imagined information based on the obtained functional information and the obtained inferred information;

interpreting the imagined information;

using the interpreted imagined information as computer command input.

* * * * *